(12) United States Patent
Waibel et al.

(10) Patent No.: US 8,263,814 B2
(45) Date of Patent: Sep. 11, 2012

(54) ENERGY EFFICIENT SEPARATION OF ETHANOL FROM AQUEOUS SOLUTION

(75) Inventors: Brian J. J. Waibel, Kennett Square, PA (US); Val J. Krukonis, Lexington, MA (US)

(73) Assignee: DynaSep Inc., Wilmington, DE (US)

( * ) Notice: Subject to any disclaimer, the term of this patent is extended or adjusted under 35 U.S.C. 154(b) by 389 days.

(21) Appl. No.: 12/300,694

(22) PCT Filed: May 15, 2008

(86) PCT No.: PCT/US2008/063677
§ 371 (c)(1),
(2), (4) Date: Jul. 24, 2009

(87) PCT Pub. No.: WO2008/147705
PCT Pub. Date: Dec. 4, 2008

(65) Prior Publication Data
US 2010/0069686 A1    Mar. 18, 2010

Related U.S. Application Data

(60) Provisional application No. 60/939,934, filed on May 24, 2007.

(51) Int. Cl.
C07C 29/74 (2006.01)
F25J 3/00 (2006.01)
(52) U.S. Cl. .......................................... 568/913; 62/617
(58) Field of Classification Search .................. 568/913; 62/617
See application file for complete search history.

(56) References Cited

U.S. PATENT DOCUMENTS

| | | |
|---|---|---|
| 2,188,051 A | 1/1940 | Lantz |
| 2,631,966 A | 3/1953 | Francis |
| 3,939,281 A | 2/1976 | Schwengers |
| 3,969,196 A | 7/1976 | Zosel |
| 4,124,528 A | 11/1978 | Modell |
| 4,346,241 A | 8/1982 | Feldman |
| 4,409,406 A | 10/1983 | Feldman |
| 4,455,198 A | 6/1984 | Zudkevitch et al. |
| 4,466,923 A | 8/1984 | Friedrich |
| 4,492,808 A | 1/1985 | Hagen et al. |
| 4,508,928 A | 4/1985 | Victor |
| 4,517,298 A | 5/1985 | Tedder |
| 4,520,213 A | 5/1985 | Victor |
| 4,624,417 A | 11/1986 | Gangi |
| 4,692,432 A | 9/1987 | Tedder |
| 4,749,495 A | 6/1988 | Schmidt |
| 4,769,112 A | 9/1988 | Wheldon |
| 4,770,780 A | 9/1988 | Moses |
| 4,842,693 A | 6/1989 | Wheldon |
| 4,865,973 A | 9/1989 | Kollerup et al. |
| 4,877,530 A | 10/1989 | Moses |
| 4,956,052 A | 9/1990 | Hirata et al. |
| 5,013,447 A | 5/1991 | Lee et al. |
| 5,036,005 A | 7/1991 | Tedder |
| 5,160,044 A | 11/1992 | Tan |
| 5,215,902 A | 6/1993 | Tedder |
| 5,284,983 A | 2/1994 | Muto et al. |
| 5,718,937 A | 2/1998 | Heidlas et al. |
| 5,932,101 A | 8/1999 | Kanel et al. |
| 6,106,720 A | 8/2000 | Kanel et al. |
| 2003/0108493 A1 | 6/2003 | Henry |

FOREIGN PATENT DOCUMENTS

| | | |
|---|---|---|
| DE | 4041097 | 6/1992 |
| DE | 10200226 | 8/2003 |
| JP | 62029988 | 2/1987 |
| JP | 63162636 | 7/1988 |

OTHER PUBLICATIONS

Groot et al., "Butanol Recovery from Fermentations by Liquid-Liquid Extraction and Membrane Solvent Extractions," 1990, Bioprocess Engineering, 5, pp. 203-216.
Mehta et al., "A Novel Extraction Process for Separating Ethanol and Water," Ind. Eng. Chem. Process Des. Dev., 1985, 24, 558-560.
Munson et al., "Factors Influencing Solvent Selection for Extraction of Ethanol from Aqueos Solutions," Ind. Eng. Chem. Process Des. Dev., 1984, 23, 109-115.
Offeman, et al., "Solvent Extraction of Ethanol from Aqueous Solutions Using Biobased Oils, Alcohols, and Esters," JAOCS, vol. 83, No. 2, (2006), 153-157.
Athanassios Z, et al., "Multiphase High Pressure Equilibria in Ternary Aqueous Systems," FluidPhase Equilibria, 29 (1986) 525-534.
Ennis, et al., "Continuous Product Recovery by In-Situ Gas Stripping/Condensation During Solvent Production From Whey Permeate Using Clostridium Acetobutylicum," Biotechnology Letters, vol. 8, No. 10 (1986) 725-730.
Laitinen and Kaunisto, "Supercritical fluid extraction of 1-butanol from aqueous solutions," Journal of Supercritical Fluids, 15 (1999) 245-252.
Qureshi and Blaschek, "Recovery of butanol from fermentation broth by gas stripping," Renewable Energy 22 (2001) 557-564.
PCT International Search Report for Application No. PCT/US08/36377, issued Aug. 8, 2008, 1 page total.
PCT Written Opinion for Application No. PCT/US08/36377, issued Aug. 8, 2008, 5 pages total.
PCT International Preliminary Report on Patentability for Application No. PCT/US08/36377, issued Nov. 24, 2009, 6 pages total.

*Primary Examiner* — Sikarl Witherspoon
(74) *Attorney, Agent, or Firm* — Weaver Austin Villeneuve and Sampson LLP

(57) ABSTRACT

The present invention provides methods and systems for extracting ethanol from an ethanol-water solution comprising (1) extracting ethanol from an ethanol-water solution with a first solvent comprising an esterified fatty acid, wherein the esterified fatty acid comprises a hydroxylated fatty acid component and an alcohol component such that the alcohol component is a $C_{3-6}$ alcohol, such that the distribution coefficient for ethanol in the mixture of the ethanol-water solution and the first solvent is at least 0.02 favoring the transfer of ethanol from the ethanol-water solution to the first solvent, thereby extracting the ethanol from the ethanol-water solution into the first solvent, and (2) extracting the ethanol-enriched first solvent with carbon dioxide, such that the carbon dioxide is at a liquid or near supercritical phase, wherein the distribution coefficient for ethanol in a mixture of the first solvent and the carbon dioxide is at least 0.1 favoring the transfer of ethanol from the first solvent to the carbon dioxide.

23 Claims, 2 Drawing Sheets

ENERGY EFFICIENT SEPARATION OF ETHANOL FROM AQUEOUS SOLUTION

CROSS-REFERENCE TO RELATED APPLICATIONS

The present invention is the U.S. National Phase entry under 35 U.S.C. §371 of International Application No. PCT/US08/63677, filed May 15, 2008, which claims priority from and the benefit of U.S. Provisional Application No. 60/939,934, filed on May 24, 2007, the entire disclosure of which is hereby incorporated herein by reference for all purposes.

FIELD OF THE INVENTION

The present invention relates to the energy efficient and selective extraction of ethanol from an aqueous solution.

BACKGROUND OF THE INVENTION

The notion of using a liquid solvent to extract ethanol from an aqueous solution has been pursued since the early 1980s. For example, in 1984, Munson and King published "Factors Influencing Solvent Selection for Extraction of Ethanol from Aqueous Solutions," Industrial and Engineering Chemistry Process Design and Development, 23, p 109-115. Munson and King examined solvents and solvent mixtures for the extraction of ethanol from dilute aqueous solutions. Results were tabulated on the basis of capacity, as represented by the distribution coefficient, and selectivity, as represented by the separation factor. Munson and King showed that an increasing distribution coefficient generally correlates with a decreasing separation factor. Thus, as the solvent become more effective for extracting ethanol, the solvent, unfortunately, becomes less effective for rejecting the water.

Previously disclosed methods of using an oil to extract ethanol from a dilute aqueous solution have proven to be energetically and economically inefficient. For example, Metha and Fraser, "A Novel Extraction Process for Separating Ethanol and Water," Industrial and Engineering Chemistry Process Design and Development, 24, 1985, p 556-560 detail a method to use light paraffin oil to extract ethanol from water. Their method leverages the ternary phase behavior of ethanol-water-paraffin oil system. The proposed process scheme requires process temperatures in the range from 30° C. to 115° C. The report does not provide the optimum process conditions. Ethanol's boiling point is 78° C. Furthermore, in order to have favorable energy input into the process, the process requires that paraffin oil travel with the discharged ethanol. Because paraffin oil is more valuable than ethanol, it is not clear that the proposed process has an economic advantage.

Numerous published methods for the extraction of ethanol require a distillation step to remove ethanol from water, which is energetically and economically inefficient, and an unnecessary additional step. For example, U.S. Pat. Nos. 4,409,406; 4,865,973; 4,770,780; 5,036,005; and 5,215,902 each disclose processes for the extraction of ethanol that require a distillation step to remove ethanol from water.

Others have also proposed using carbon dioxide as a primary extractant of ethanol from an aqueous solution. However, these methods are limited by the distribution coefficient between ethanol-water and $CO_2$ that has been measured to be on the order of 0.1 by numerous researchers, e.g. Krukonis (FIG. 8.11, p. 173, McHugh, M., Krukonis, V., *Supercritical Fluid Extraction*, 2nd Ed., Butterworth-Heinemann, 1994). These processes have no energy advantage over a traditional binary distillation process. See, for example, U.S. Pat. Nos. 4,842,693; 5,160,044; and 4,770,780.

There remains a need for an energetically and economically favorable extraction of ethanol from dilute aqueous solutions. The present invention addresses this and other needs.

BRIEF SUMMARY OF THE INVENTION

The present invention provides methods and systems for extracting ethanol from an ethanol-water solution. In some embodiments, the methods comprise:

a) mixing an ethanol-water solution with a first solvent comprising an esterified fatty acid, wherein the esterified fatty acid comprises a hydroxylated fatty acid component and an alcohol component such that the alcohol component is a C3-6 alcohol, wherein the distribution coefficient for ethanol in the mixture of the ethanol-water solution and the first solvent is at least 0.02 favoring the transfer of ethanol from the ethanol-water solution to the first solvent, thereby extracting the ethanol from the ethanol-water solution into the first solvent;

b) separating the first solvent and the ethanol-water solution;

c) contacting the first solvent with carbon dioxide, wherein the carbon dioxide is at a liquid or near supercritical phase, wherein the distribution coefficient for ethanol in a mixture of the first solvent and the carbon dioxide is at least 0.1 favoring the transfer of ethanol from the first solvent to the carbon dioxide, thereby extracting the ethanol from the first solvent into the carbon dioxide; and d) converting the carbon dioxide to vapor phase, thereby releasing the ethanol from the carbon dioxide, yielding a solution of greater ethanol concentration than the ethanol concentration in the starting ethanol-water solution. In some embodiments, a substantially pure ethanol solution is yielded.

In some embodiments, the ethanol-water solution comprises less than 99% ethanol (v/v). In some embodiments, the ethanol-water solution is a dilute ethanol solution. In some embodiments, the ethanol-water solution is a fermentation broth.

In some embodiments, the hydroxylated fatty acid component of the esterified fatty acid is ricinoleic acid. In some embodiments, the esterified fatty acid is a triglyceride. In some embodiments, the triglyceride comprises 1 to 3 ricinoleic acid substituents.

In some embodiments, the alcohol component is glycerol.
In some embodiments, the first solvent is castor oil.
In some embodiments, the first solvent is contacted with the carbon dioxide in a counter current column.

In some embodiments, the ethanol is extracted without a distillation step to remove ethanol from water, i.e., no distillation of the ethanol-water stream.

In a further aspect, the invention provides systems for extracting ethanol from an ethanol-water solution. In some embodiments, the systems comprise:

a liquid feed inlet to receive the ethanol-water solution and a first solvent;

a mixer configured to continuously mix the ethanol-water solution and the first solvent, wherein the ethanol-water solution comprises ethanol and the first solvent comprises an esterified fatty acid, wherein the esterified fatty acid comprises a hydroxylated fatty acid component and an alcohol component such that the alcohol component is a C3-6 alcohol, wherein the distribution coefficient for ethanol in the mixture of the ethanol-water solution and the first solvent is at least 0.02 favoring the transfer of ethanol from the ethanol-water solution to the first solvent, thereby extracting the ethanol from the ethanol-water solution into the first solvent, the liquid feed inlet being configured for fluid communication with the mixer;

a separation vessel, being configured for fluid communication with the mixer;

an extraction vessel configured to extract the ethanol with carbon dioxide, wherein the carbon dioxide is at a liquid or near supercritical phase, wherein the distribution coefficient for ethanol in a mixture of the first solvent and the carbon dioxide is at least 0.1 favoring the transfer of ethanol from the first solvent to the carbon dioxide, thereby extracting the ethanol from the first solvent into the carbon dioxide, the extraction vessel being configured for fluid communication with the separation vessel;

a vaporizer configured to convert the carbon dioxide to vapor phase, thereby releasing the ethanol from the carbon dioxide, whereby the ethanol is extracted from the ethanol-water solution, the vaporizer being configured for fluid communication with the extraction vessel; and a collector configured to receive the ethanol, the collector being configured for fluid communication with the vaporizer.

In some embodiments, the ethanol-water solution is a fermentation broth.

In some embodiments, the liquid feed inlet is selected from the group consisting of hose, piping and tubing.

In some embodiments, the mixer is an in-line mixer.

In some embodiments, the separation vessel is a centrifuge.

In some embodiments, the extraction vessel is a counter-current column.

In some embodiments, the vaporizer further comprises a heat pump for the vaporization and recovery of liquid carbon dioxide.

In some embodiments, the collector is a cyclone separator.

In some embodiments, the separation vessel is in fluid communication with the liquid feed inlet for recycling the ethanol-water solution. In some embodiments, the extraction vessel is in fluid communication with the liquid feed inlet for recycling the first solvent.

In some embodiments, the system further comprises a condenser to convert the vapor phase carbon dioxide to the liquid or near supercritical phase, the condenser being configured for fluid communication with the collector.

In some embodiments, the condenser is in fluid communication with the extraction vessel for recycling the carbon dioxide.

In some embodiments, the system allows for continuous flow processing.

In some embodiments, the ethanol is extracted without a distillation step to remove ethanol from water, i.e., no distillation of the ethanol-water stream.

Definitions

As used herein, the term "hydroxylated fatty acid" refers to a carboxylic acid having 8 to 30 carbons and substituted with one or more hydroxy groups. Hydroxylated fatty acids can be saturated, mono-unsaturated or poly-unsaturated. Hydroxylated fatty acids useful in the present invention also include branched hydroxylated fatty acids such as iso-fatty acids. Examples of hydroxylated fatty acids useful in the present invention, include, but are not limited to, hydroxylated versions of the following fatty acids: capric acid (C10), lauric acid (C12), myristic acid (C14), palmitic acid (C16), palmitoleic acid (C16), stearic acid (C18), isostearic acid (C18), oleic acid (C18), vaccenic acid (C18), linoleic acid (C18), alpha-linoleic acid (C18), gamma-linolenic acid (C18), arachidic acid (C20), gadoleic acid (C20), arachidonic acid (C20), eicosapentaenoic acid (C20), behenic acid (C22), erucic acid (C22), docosahexaenoic acid (C22), lignoceric acid (C24) and hexacosanoic acid (C26). Other examples of hydroxylated fatty acids useful in the present invention include, but are not limited to, ricinoleic acid, dimorphecolic acid, hydroxy-hexadecanoic acid and hydroxy-docosanoic acid. The hydroxylated fatty acids of the present invention can also be substituted with groups such as epoxy, ether, keto and ester.

The term "alcohol component" refers to a straight or branched, saturated, radical having 3-10 carbon atoms and one or more hydroxy groups. The alkyl portion of the alcohol component can be propyl, butyl, pentyl, hexyl, iso-propyl, iso-butyl, sec-butyl, tert-butyl, etc. Alcohol components useful in the present invention include, but are not limited to, propanol, isopropanol, glycerol, butanol, isobutanol, t-butanol, pentanol and hexanol, among others. One of skill in the art will appreciate that other alcohol components are useful in the present invention.

The term "esterified fatty acid" refers to a hydroxylated fatty acid, as defined above, that has been esterified with an alcohol component, as defined above. The alcohol component can have one or more hydroxyl groups, and thus can esterify one or more hydroxylated fatty acids. One example of an esterified fatty acid of the present invention is a triglyceride, a glycerol esterified with three hydroxylated fatty acids. The hydroxylated fatty acid component of the esterified fatty acids of the present invention include, but are not limited to, hydroxylated fatty acids such as ricinoleic acid. Examples of esterified fatty acids of the present invention include compounds of Formula I:

(I)

wherein radical l is an integer of from 1 to 4, including, 1, 2, 3 and 4, and radicals m and n are separately integers of from 1 to 26, wherein the sum of m and n is at least 5 and no more than 27. As described above, the alcohol component of the esterified fatty acid can have additional hydroxy substituents. As described above, the hydroxylated fatty acid component of the esterified fatty acids of the present invention can have additional hydroxy substituents, be branched or unbranched, and be saturated or unsaturated. Esterified fatty acids of the present invention also include triglyceride compounds of Formula II:

(II)

wherein radicals m, m', m", n, n' and n" are separately integers of from 1 to 26, wherein the sum of m and n, the sum of m' and n', and the sum of m" and n" is each separately at least 5 and no more than 27. Additional examples of esterified fatty acids of the present invention include esters of ricinoleic acid, such as in castor oil. One of skill in the art will appreciate that other esterified fatty acids are useful in the present invention.

The term "first solvent" refers to a solvent capable of extracting the ethanol from the ethanol-water solution. The first solvent is preferably such that the ethanol has a distribution coefficient of at least 0.02, favoring the transfer of ethanol to the first solvent, and where the ethanol has a distribution coefficient of at least 0.1 favoring the transfer of ethanol from the first solvent to the carbon dioxide. The first solvent comprises an esterified fatty acid, wherein the esterified fatty acid comprises a hydroxylated fatty acid, as described above. Solvents useful as the first solvent of the present invention are those solvents having a high percentage of a hydroxylated fatty acid. One example of a suitable first solvent in the present invention is castor oil, having a composition of from about 85 to 95% ricinoleic acid. One of skill in the art will appreciate that other solvents are useful in the present invention.

The terms "extraction," "extracting" and "extracted" interchangeably refer to the process of drawing one component of a mixture into another mixture. In the present invention, the ethanol of the ethanol-water solution is first drawn from the ethanol-water solution into the first solvent of esterified fatty acid, and then from the first solvent of the esterified fatty acid into the carbon dioxide.

The phrase "converting to vapor phase" refers to the step of altering the temperature and pressure of the carbon dioxide apparatus to change the phase of the carbon dioxide from liquid phase or near supercritical phase to the vapor phase.

The term "liquid phase" refers to carbon dioxide under the appropriate temperature and pressure conditions in order to form a liquid phase. Provided the temperature and pressure are below the critical point for carbon dioxide (30.978° C. and 73.773 bar), the liquid phase of carbon dioxide can be achieved through pressure alone, temperature alone, or through a combination of temperature and pressure. One of skill in the art will know what temperature and pressure are appropriate to form the liquid phase of carbon dioxide.

The term "supercritical phase" refers to carbon dioxide under the appropriate temperature and pressure conditions in order to form a supercritical phase or near supercritical phase. This exists at a temperature and pressure that exceeds the critical temperature of 30.978° C. and critical pressure of 73.773 bar. One of skill in the art will know what temperature and pressure are appropriate to form the supercritical phase of carbon dioxide.

The term "recycle" refers to the processing of materials so that the materials can be used again. Following extraction of the ethanol and vaporization, the carbon dioxide is condensed back to the liquid phase and returned to the step of ethanol extraction with carbon dioxide. The recycling prevents resources from being wasted, reduces the consumption of raw materials and reduces energy usage.

The term "reuse" refers to the act of using for a subsequent time, an item that has already been used and discarded. In the present invention, the carbon dioxide used in the extraction is converted to the vapor phase in order to separate the ethanol. The vapor phase carbon dioxide is recycled via condensation and supplied back to the extraction apparatus, thus being used again to extract additional ethanol from the first solvent.

The term "countercurrent column" refers to a column in which liquid-liquid separation occurs using countercurrent techniques. One of skill in the art will appreciate which countercurrent techniques are useful in the methods of the present invention.

The term "distribution coefficient" refers to the ratio of concentrations of all forms of a compound (ionized and unionized) in the two phases of a mixture of two immiscible solvents at equilibrium. See, Leo, et al., *Chem Rev* (1971) 71(6):525-616. The distribution coefficient can be used as a measure of how hydrophilic or hydrophobic a chemical substance is. The distribution coefficient describes the pH-dependent hydrophobicity of compounds, and is related to P (the partition coefficient), which describes the hydrophobicity of neutral (i.e., unionized) compounds only. The distribution coefficient can be symbolized as "K" or "D." D (or K) is the ratio of the sum of concentrations of the solute's (e.g., ethanol, castor oil) various forms in one solvent, to the sum of the concentrations of the solute's forms in the other solvent, where the units of the concentration can be weight percent, mole percent, or g/mL, and can be calculated by the following equation:

$$D_{organic/water} = [solute]_{organic}/[solute]_{water}$$

The distribution coefficient can be measured using any method known in the art. Exemplified methods include (i) the shake flask or tube method and (ii) high performance liquid chromatography (HPLC) or gas chromatography (GC). In the shake flask method, the solute in question is diluted or dissolved to equilibrium in equal volumes of a mixture of organic phase solvent and water phase solvent, then the concentration of the solute in each solvent is measured, for example, by HPLC, GC, UV/VIS spectroscopy. In HPLC, the D of a solute can be determined by correlating its retention time with similar compounds with known D values.

The term "separation factor" refers to a measure of the fold-difference or ratio of two different distribution coefficients in self-consistent units. A separation factor can be symbolized as "α" and is calculated by dividing one distribution ratio by another. The separation factor is a measure of the ability of a system to separate two solutes.

The phrase "continuous flow process" refers to a process having constant input and output. For example, when a fermentation is not rendered toxic by the solvent, the fermentation will continuously produce ethanol, which can be siphoned into an extraction process. The siphoning off of ethanol maintains a low concentration of ethanol allowing fermentation to continue indefinitely. A continuous flow process is in contrast to a process that requires batch or discontinuous processing.

The phrase "ethanol-water solution" refers to a solution comprising water and ethanol. The solution can comprise up to about 99% (v/v) ethanol, e.g., about 99%, 97%, 95%, 90%, 80%, 70%, 60%, 50%, 40%, 30%, 25%, 20%, 15%, 10%, 9%, 8%, 7%, 6%, 5%, 4%, 3%, 2% or 1% (v/v) ethanol. One of skill in the art will appreciate that other amounts of ethanol are possible in the ethanol-water solutions of the present invention.

The phrase "dilute ethanol-water solution" refers to a solution comprising water and about 20% (v/v) or less of ethanol, for example, about 15%, 10%, 5%, 4%, 3%, 2% or 1% (v/v), or less of ethanol.

A "substantially pure ethanol solution" refers to a solution comprising at least 99% ethanol.

A "solution of greater ethanol concentration" refers to a solution of ethanol that has been subjected to an extraction process of the invention with a detectably greater concentration of ethanol in comparison to the feedstock solution of ethanol. Determination of ethanol concentrations in an ethanol solution (e.g., an ethanol-water solution) are well known in the art. Ethanol concentrations can be determined using any method known in the art, including for example, gas chromatography or Karl-Fischer titration analysis. The amount of change in concentration will typically depend on the concentration of ethanol in the feedstock solution. Extraction of a feedstock ethanol-water solution of low ethanol concentration will result in an end product with a relatively larger amount of ethanol concentration. Known assays can detect ethanol concentration changes of at least about 0.1%. Using the extraction methods of the invention, the end product solution can have an ethanol concentration that is at least about 0.1%, for example at least about 0.5%, 1%, 2%, 5%, 10%, 20%, 30% greater than the feedstock ethanol-water solution.

The phrase "fluid communication" refers to at least two elements that are connected in such a way to allow for the free flow of a fluid medium from the one element to the second element. Two elements can optionally be connected by a controller (e.g., a valve) of the flow of the fluid medium.

DETAILED DESCRIPTION

I. Introduction

This invention is a process for efficiently separating ethanol from an dilute solution of ethanol in water. The separation is achieved by first using a primary fatty acid solvent, for example a triglyceride fatty acid solvent, which has the characteristics of a favorable distribution coefficient for ethanol between the aqueous solution and the organic solvent and is non-toxic to a fermentation bath. Castor oil or ricinoleic acid possess these characteristics. In addition, the first solvent has the added benefit of being non-toxic to the fermentation broth.

When combined with an ethanol-water solution, the first solvent dissolves a portion of the ethanol present and a more limited portion of the water present. The first solvent phase contains fatty acid solvent, ethanol, and water. The first solvent phase is separated from the aqueous phase. This first solvent phase containing ethanol is then mixed with carbon dioxide at subcritical or supercritical conditions near the critical point. At these process conditions, carbon dioxide has a very favorable distribution coefficient for the ethanol and a very unfavorable distribution coefficient for the fatty acid and the water. This enables a small solvent to feed ratio ($CO_2$ mass to solvent stream mass) to be used to dissolve the ethanol from the organic solvent. The $CO_2$ stream is separated from the organic phase. The $CO_2$ pressure and temperature is adjusted so that the $CO_2$ can be converted to the vapor phase and the liquid ethanol can be recovered. This invention provides a means to more energy efficiently separate the dilute ethanol from water (as is typical of a fermentation bath) and to break the ethanol-water azeotrope. The methods of the invention can extract substantially pure ethanol and pure ethanol from an aqueous solution in an energetically and economically favorable manner and without the need for distillation of ethanol from water.

II. Methods for Energy Efficient Extraction of Ethanol

The present invention provides methods for the extraction of ethanol from an ethanol-water solution in an energy efficient manner that breaks the water-ethanol azeotrope, providing substantially pure ethanol (e.g., near 100%, for example about 98% or 99% pure). The methods of the present invention are able to break the azeotrope by first extracting the ethanol from an ethanol-water solution using a first solvent comprising an ester of a hydroxylated fatty acid, and then extracting the ethanol from the ester of the hydroxylated fatty acid using liquid or near supercritical carbon dioxide. In order for the extraction to favor the ester of the hydroxylated fatty acid and then the carbon dioxide, ethanol must have a favorable distribution coefficient for the ester of the hydroxylated fatty acid over water, and then for carbon dioxide over the ester of the hydroxylated fatty acid. By employing first and second solvents with favorable distribution coefficients for ethanol and high separation factors for the discarded phase, the present methods provide energetically and economically advantageous processes.

In preferred embodiments, the methods of the invention are performed as a continuous flow process, wherein materials are continuously flowing from one step to the next, or from one element to the next in the present systems. In some embodiments, materials (e.g., the first and second solvents) are recycled and reused. The recycling and reuse of materials provides several energy savings. Additional energy savings derive from the lack of a distillation step in the separation of the ethanol from water and the ester of the hydroxylated fatty acid. Instead of an energy inefficient process requiring distillation of ethanol from water, the present invention uses liquid carbon dioxide to extract the ethanol. The carbon dioxide containing ethanol is then vaporized to separate the ethanol, followed by recondensation of the carbon dioxide in order to recycle and reuse the carbon dioxide. The total energy required to achieve the ethanol separation from water is much less than that required by conventional distillation and dehydration via molecular sieve. Accordingly, the methods of the present invention provide an energy efficient process for extracting ethanol from an ethanol-water solution.

1. Mixing An Ethanol-Water Solution With A First Solvent Comprising An Esterified Fatty Acid a. First Solvent Comprising an Esterified Fatty Acid The first step of the methods involve mixing an ethanol-water solution with a first solvent comprising an esterified fatty acid. The ethanol-water solution can be any aqueous solution comprising ethanol. The ethanol-water solution can also be a fermentation broth such as from the fermentation of fruits, vegetables (e.g., corn and potatoes), grains and cellulose. The ethanol-water solution can comprise up to about 99% (v/v) ethanol, e.g., 99%, 97%, 95%, 90%, 80%, 70%, 60%, 50%, 40%, 30%, 25%, 20%, 15%, 10%, 9%, 8%, 7%, 6%, 5%, 4%, 3%, 2% or 1% ethanol. In some embodiments, the ethanol-water solution is a dilute ethanol solution comprising about 20% (v/v) or less of ethanol, for example about 20%, 15%, 10%, 9%, 8%, 7%, 6%, 5%, 4%, 3%, 2% or 1% ethanol. The ethanol-water solution can be from fresh feedstock, for example, from the fermentation broth, and can be from recycling ethanol-water solution and first solvent that is discarded during later portions of the system.

The first solvent of the method of the present invention comprises an esterified fatty acid. The esterified fatty acid of the first solvent comprises an alcohol component and a hydroxylated fatty acid component. The alcohol component can be any alcohol, preferably a $C_{3-6}$ alcohol. The alcohol component can be substituted with another hydroxy, an ether and an ester. The alcohol component can have more than one hydroxy group. When the alcohol component has three hydroxy groups, the alcohol component can be glycerol.

The hydroxylated fatty acid component of the esterified fatty acid comprises one or more hydroxy groups on fatty acids such as capric acid (C10), lauric acid (C12), myristic acid (C14), palmitic acid (C16), palmitoleic acid (C16), stearic acid (C18), isostearic acid (C18), oleic acid (C18), vaccenic acid (C18), linoleic acid (C18), alpha-linoleic acid (C18), gamma-linolenic acid (C18), arachidic acid (C20), gadoleic acid (C20), arachidonic acid (C20), eicosapentaenoic acid (C20), behenic acid (C22), erucic acid (C22), docosahexaenoic acid (C22), lignoceric acid (C24) and hexacosanoic acid (C26). The hydroxy groups are preferably at the C3 position or greater. More preferably, the hydroxy groups are at the C7 position or greater. Most preferably, the hydroxy group are at the C11 position or greater. The hydroxylated fatty acids of the present invention are can be saturated, mono-unsaturated or poly-unsaturated. In addition, the hydroxylated fatty acids of the present invention can be branched or straight-chain. The hydroxylated fatty acids of the present invention can also be substituted with groups such as epoxy, ether, keto and ester. Other examples of hydroxylated fatty acids useful in the present invention include, but are not limited to, ricinoleic acid, dimorphecolic acid, hydroxy-hexadecanoic acid and hydroxy-docosanoic acid.

Esterified fatty acids of the present invention are available commercially from a variety of commercial sources including Sigma-Aldrich (Milwaukee, Wis.), Fischer Scientific (Waltham, Mass.) and AcrosOrganics (Geel, Belgium). Alternatively, the esterified fatty acids of the present invention can be prepared from a suitable alcohol component and a suitable hydroxylated fatty acid component under esterifying conditions known to one of skill in the art.

The composition of the first solvent is such that the distribution coefficient for ethanol in the mixture of the ethanol-water solution and the esterified fatty acid is at least 0.02 (wt. %), for example, 0.04, 0.06, 0.08, 0.10, favoring the transfer of ethanol from the ethanol-water solution to the first solvent, and at least 0.1 (wt. %), for example, 0.2, 0.3, 0.4, 0.5, favoring the transfer of ethanol from the first solvent to the carbon dioxide.

In some embodiments, the first solvent comprises a triglyceride wherein at least one of the fatty acid components of the triglyceride is a hydroxylated fatty acid, including those described above. The triglyceride can also have all three fatty acid components be hydroxylated fatty acids. In some embodiments, the hydroxylated fatty acid is ricinoleic acid. The triglycerides of the present invention can be prepared from glycerol and suitable fatty acid components, including at least one hydroxylated fatty acid component, under esterifying conditions known to one of skill in the art.

The triglycerides of the present invention are such that ethanol has similar distribution coefficients to those described above.

In some embodiments, the first solvent of the present invention is castor oil. Castor oil can be purchased from a variety of commercial sources including JODL Inc. (Warminster, Pa.), Sigma-Aldrich (Milwaukee, Wis.), Fischer Scientific (Waltham, Mass.) and AcrosOrganics (Geel, Belgium). Commercial grade castor oil is sufficient for the process.

b. Mixing the Ethanol-Water Solution with the First Solvent

The mixing of the ethanol-water solution and the first solvent can be accomplished using any known means for mixing including those discussed below. In some embodiments, the mixing of the ethanol-water solution and the first solvent of the present invention is accomplished using an in-line mixer. The mixing is typically carried out at ambient temperature, for example in the range of about 20-35° C., for example, about 25-30° C., but can be performed at superambient (i.e., temperatures requiring heat input) or subambient (i.e., temperatures requiring cooling input) temperatures. Mixing is performed for an amount of time to sufficient to uniformly mix the ethanol-water phase and the first solvent phase.

2. Separating the First Solvent and the Ethanol-Water Solution

The first solvent and the ethanol-water solution can be separated by any known method in the art. Separation can be accomplished, for example, by density, magnetic properties or electrical characteristics. Separation by density, for example, can be accomplished using any method known in the art, for example, a centrifuge, a funnel, and the like. The oil-rich phase is less dense than the water-rich phase.

After separation of the first solvent and the ethanol-water solution, the ethanol-enriched first solvent is recovered for further extraction of the ethanol in a second solvent, carbon dioxide. The ethanol-water solution can be discarded or can be returned to the fermentation broth. Recycled ethanol-water solution (i.e., ethanol-water solution that has been subject to at least one extraction) can be pooled with unextracted (i.e., "fresh") ethanol-water solution before being exposed to further extraction with the first solvent.

3. Contacting the First Solvent with the Second Solvent, Carbon Dioxide

Following separation from the ethanol-water solution, the ethanol-enriched first solvent is contacted with a second solvent, carbon dioxide. The carbon dioxide can be in any phase suitable for extraction of the ethanol from the first solvent. Depending on the pressure and temperature, carbon dioxide can exist in any of several different phases, e.g. vapor phase, liquid phase, near supercritical phase, or supercritical phase, and dry ice, among others. The carbon dioxide is in a phase such that the distribution coefficient for ethanol in a mixture of the first solvent and the $CO_2$ is at least 0.1 favoring the transfer of ethanol from the esterified fatty acid to the $CO_2$. In some embodiments, the carbon dioxide can be in a liquid phase or near supercritical phase in order to extract the ethanol from the first solvent and into the carbon dioxide.

The ethanol is extracted into the carbon dioxide using any known means in the art. In some embodiments, the ethanol can be extracted by the carbon dioxide using a countercurrent column (CC), such as described below.

In order to maintain the carbon dioxide in the appropriate liquid phase or near supercritical phase, the vessel (e.g., countercurrent column) is maintained at the appropriate temperature and pressure. Following extraction, the first solvent is separated from the ethanol enriched carbon dioxide. In some embodiments, the first solvent is recycled back to the mixer that is mixing the first solvent and ethanol-water solution. Using this strategy, any ethanol not extracted from the first solvent by the carbon dioxide, can be reintroduced into the system so that later exposure to carbon dioxide can extract the ethanol. The recycling of the first solvent allows the first solvent to be reused, and reduces the loss of the first solvent.

4. Separating the Ethanol from the Carbon Dioxide

The ethanol enriched carbon dioxide is then separated from the ethanol using any means known in the art. For example, the carbon dioxide can be separated via vaporization. Vaporization is accomplished by changing the temperature and pressure in order to change the carbon dioxide from the liquid or near supercritical phase to the vapor phase. Preferably separation of ethanol is accomplished with minimal heat input. For example, separation of the ethanol from the carbon dioxide can be accomplished by maintaining the pressure of the carbon dioxide a few bar below the critical point (e.g., 68, 69, 70, 71, or 72 bar) and heating the process stream. At the critical point, the heat of vaporization of carbon dioxide is zero. At pressures infinitesimally below the critical point, the heat of vaporization of carbon dioxide is low and much, much lower than the heat of vaporization of water.

The ethanol can be collected using any means known in the art. For example, the ethanol can be collected using a cyclone separator during the vaporization of the carbon dioxide, as in the present invention. Membrane filtration techniques are also possible. Other suitable methods for collecting ethanol are known.

Carbon dioxide that has been vaporized can be collected, condensed back to the appropriate phase by changing the temperature and pressure, and then reinjected into the countercurrent column. The recycling of the carbon dioxide allows the carbon dioxide to be reused. The energy efficiency of the vaporization-condensation cycle of the recycled carbon dioxide can be increased by the concurrent use of a heat pump.

Through the combination of the castor oil extraction and carbon dioxide extraction using the countercurrent column, the method of the present invention breaks the water-ethanol azeotrope. In preferred embodiments, the ethanol is separated from the carbon dioxide without requiring distillation of ethanol or water.

III. Systems

Figure 1:
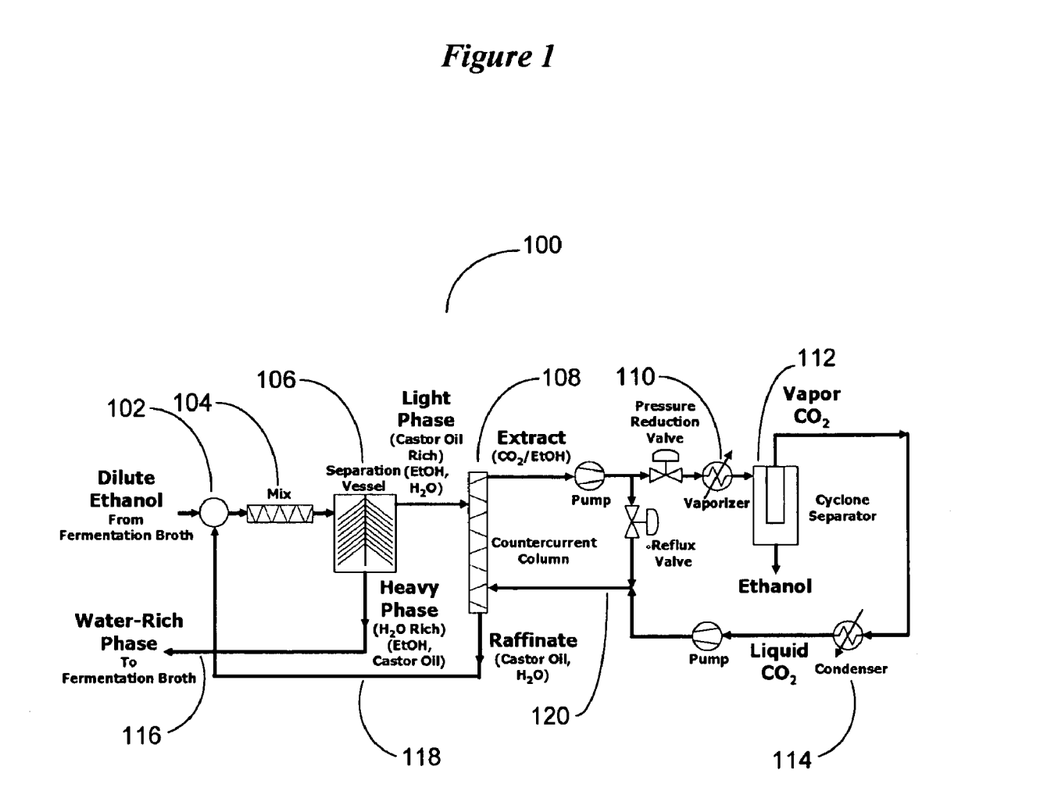
FIG. 1 illustrates one embodiment of the present methods for extracting ethanol from an ethanol-water solution.
Figure 2:
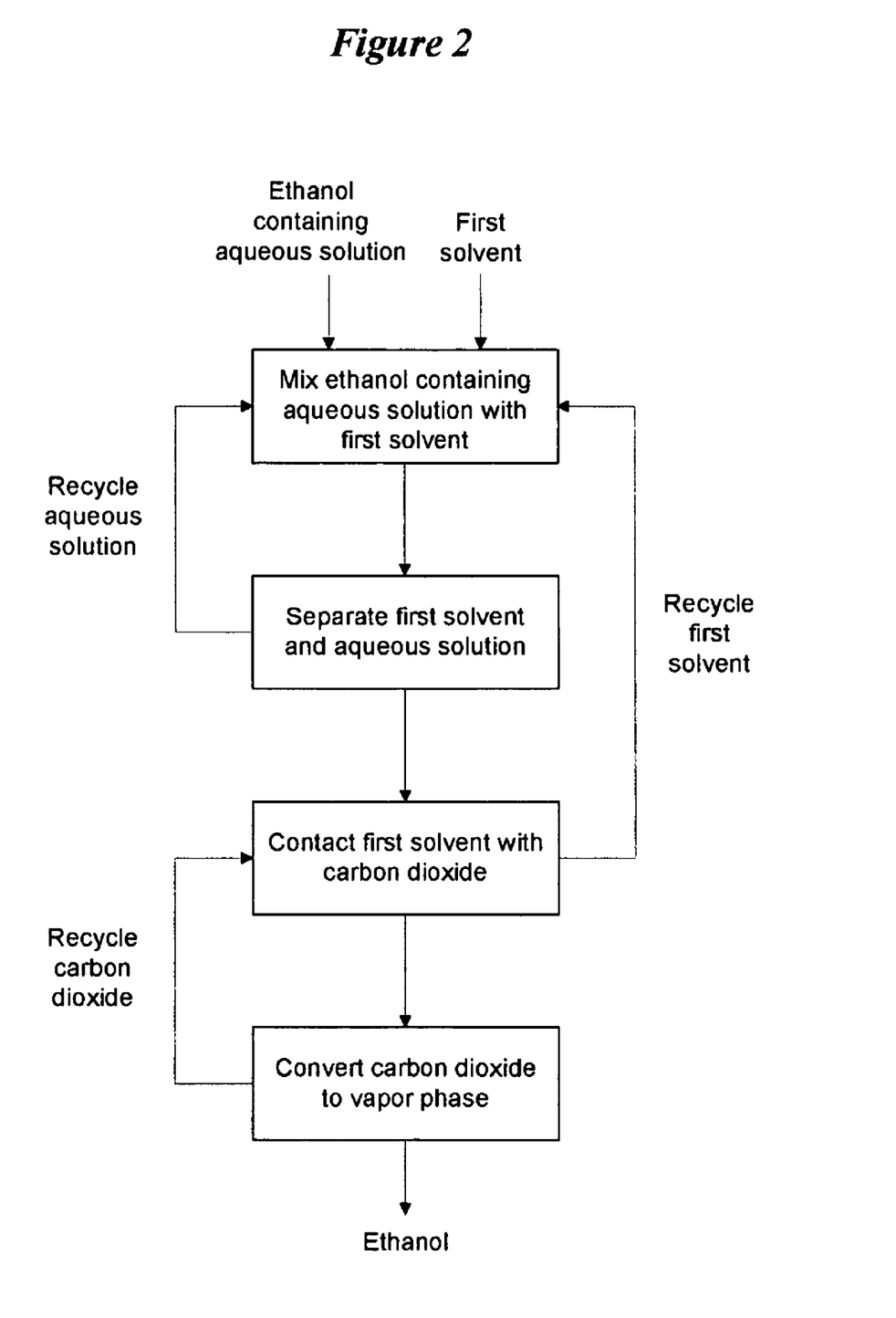
FIG. 2 illustrates a flow chart of the processes of the present invention.

FIG. 1 shows one embodiment of a system, 100, for extracting ethanol from an ethanol-water solution. The system comprises a liquid feed inlet for receiving the ethanol-water solution and a first solvent, a mixer configured to continuously mix the ethanol-water solution with the first solvent, a separation vessel for separating the first solvent and the ethanol-water solution, an extraction vessel configured to extract the ethanol with carbon dioxide, a vaporizer for converting the carbon dioxide to vapor phase, and a collector configured to receive the ethanol.

The system of the present invention extracts ethanol from an ethanol-water solution by breaking the water-ethanol azeotrope and providing ethanol of near 100% purity. In preferred embodiments, the systems of the invention allow for a continuous flow process, wherein materials are continuously flowing from one step of the system to the next. The systems preferably allow for the recycling and reuse of the first and second solvents. The recycling and reuse of materials provides several energy savings. Additional energy savings stem from the lack of a distillation step in the separation of the ethanol from water and the ester of the hydroxylated fatty acid. Instead of an energy inefficient process such as distillation, the present invention uses liquid carbon dioxide to extract the ethanol. The carbon dioxide-containing ethanol is then vaporized to separate the ethanol, followed by recondensation of the carbon dioxide in order to recycle and reuse the carbon dioxide. Accordingly, the system of the present invention provides an energy efficient process for extracting ethanol from an ethanol-water solution.

The ethanol-water solution is typically a fermentation broth, for example, from the fermentation of fruits and/or vegetables. In particular, corn is useful to prepare the fermentation broth of the present invention. The ethanol is extracted from the ethanol-water solution through the use of a first solvent.

The first solvent (see additional description above) of the system of the present invention comprises an esterified fatty acid. The esterified fatty acid of the first solvent comprises an alcohol component an a hydroxylated fatty acid component. The alcohol component can be any alcohol, preferably a $C_{3-6}$ alcohol. The alcohol component can be substituted with another hydroxy, an ether and an ester. The alcohol component can have more than one hydroxy group. When the alcohol component has three hydroxy groups, the alcohol component can be glycerol. In some embodiments, the first solvent is castor oil.

The ethanol-water solution and the first solvent are provided to the system of the present invention via a liquid feed inlet, 102, such as piping, hosing, tubing, reservoirs. The ethanol-water solution can be fresh feedstock, for example, from the fermentation broth, and can be from recycling ethanol-water solution and first solvent that is discarded during later portions of the system. One of skill in the art will appreciate that other input means are useful in the present invention.

The ethanol-water solution and first solvent are mixed in a mixer, 104, using any known means for mixing. Mixing can be accomplished using mechanical means such as paddles and a motor. Mixing can also be accomplished using static mixers. Static mixers, or motionless mixers, are fins, obstructions, or channels mounted in pipes, designed to promote mixing as fluid flows through the mixer. Most static mixers use some method of first dividing the flow, then rotating, channeling, or diverting the flow, before recombining it. Other static mixers create additional turbulence to enhance mixing.

In some embodiments, the mixing of the ethanol-water solution and the first solvent of the present invention is accomplished using an in-line mixer. Other mixers can be used, such as those described above. The mixing can be performed at a variety of temperatures and pressures, e.g., ambient temperature and pressure. In addition, the mixing can be performed for any amount of time, depending on the degree of mixing desired, such as mixing to homogeneity, in order to allow extraction of the ethanol by the first solvent from the ethanol-water solution.

The first solvent and the ethanol-water solution are then separated in separation vessel 106, using any known method in the art. Separation can be accomplished by differences in density. Separation by density, for example, can be accomplished using a centrifuge. In the centrifuge, the lighter phase of the first solvent and ethanol rises to the top where it is recovered and forwarded to the second extraction step. Alternate embodiments that could be utilized are settling tanks or hydrocyclone separators. The heavier phase of the aqueous solution and ethanol, is separated and recycled back to the mixer where it is mixed with additional fermentation broth and in order to continue removing ethanol from the ethanol-water solution, 116. Recycling of the ethanol-water solution allows continued extraction of the remaining ethanol from the ethanol-water solution in order to increase the amount of ethanol extracted from the ethanol-water solution.

Following separation from the ethanol-water solution, the ethanol enriched first solvent is placed in extraction vessel 108 where the first solvent is contacted with carbon dioxide in a liquid phase, or near a supercritical phase. The carbon dioxide is in a phase such that the distribution coefficient for ethanol in a mixture of the first solvent and the $CO_2$ is at least 0.1 favoring the transfer of ethanol from the esterified fatty acid to the $CO_2$, thereby facilitating extraction of the ethanol from the first solvent by the carbon dioxide. The phase of the carbon dioxide can be controlled by the appropriate selection of temperature and pressure.

The ethanol is extracted into the carbon dioxide using any known means in the art. For example, the ethanol can be extracted by the carbon dioxide using countercurrent column (CC). Within the CC, one can consider that three processes are occurring in conjunction: mixing, coalescing, and separation (although they often occur continuously). Mixing of the phases is necessary so that the interface between them has a large area, and the analyte can move between the phases according to its partition coefficient. The mobile phase is mixing with and then settling from the stationary phase throughout the column.

In order to maintain the carbon dioxide in the appropriate liquid or near supercritical phase, the countercurrent column is maintained at the appropriate temperature and pressure. Within the countercurrent column, the castor oil-rich phase 118 moves down the column and the carbon dioxide-rich phase 109 rises within the column. After passage through the countercurrent column, castor oil phase 118 has been depleted of ethanol and the carbon dioxide phase 109 has been enriched with ethanol. The depleted castor oil phase 118 can be returned for blending with dilute ethanol solution. All or a portion of the carbon dioxide phase can be subject to vaporization to separate the ethanol from the carbon dioxide. In some embodiments, this carbon dioxide stream can be reintroduced into the column through a reflux valve. The recycling of the first solvent allows the first solvent to be reused and increases the efficient use of the first solvent.

The use of the countercurrent chromatography breaks the water-ethanol azeotrope and enables the system of the present invention to extract ethanol at close to 100% purity.

The carbon dioxide is then separated from the ethanol in vaporizer 110, by converting the carbon dioxide to the vapor phase and collecting liquid ethanol in collector 112. Any separation means are useful in the system of the present invention. For example, the carbon dioxide can be separated via vaporization. Vaporization is accomplished by changing the temperature and pressure in order to change the carbon dioxide from the liquid or near supercritical phase to the vapor phase.

The ethanol is collected using collector 112. The collector can be a cyclone separator, among others.

Carbon dioxide that has been vaporized is recycled by first condensing the vaporized carbon dioxide using condenser 114 by changing the temperature and pressure. Condensation of the carbon dioxide is followed by reinjecting the carbon dioxide into the extraction vessel via 120. The recycling of the carbon dioxide allows the carbon dioxide to be reused, and minimizes the energy required for the extraction by minimizing materials used and energy consumed.

Through the combination of the castor oil extraction and carbon dioxide extraction using the countercurrent column, the method of the present invention breaks the water-ethanol azeotrope without requiring any distillation of ethanol or water. Furthermore, the inclusion of a heat pump in the carbon dioxide vaporization provides added energy efficiencies in the vaporization and condensation cycle.

EXAMPLES

The following examples are offered to illustrate, but not to limit the claimed invention.

Example 1

Extraction of Ethanol from An Ethanol-Water Solution

The exemplified process describes the adsorption of ethanol into castor oil and the subsequent extraction of the ethanol from the castor oil with near-critical carbon dioxide.

Referring to FIG. 1, a dilute ethanol-water solution from a fermination broth is combined with the recycled water from the first stage separator (centrifuge) and the castor oil saturated with water. The ethanol-water solution would nominally be in the range of 3 to 8 wt % ethanol in water. The recycled water will retain ethanol and some castor oil. The stream of ethanol water and castor oil is well-mixed and then subsequently separated into a light phase and heavy phase. While a settling tank separator could be employed, process economics favor the use of a centrifuge to accelerate the phase separation. The heavy phase is primarily water with some remaining ethanol and an inevitable contamination of castor oil.

The heavy phase is returned to the fermination broth. The light phase is castor oil rich with ethanol and water in solution. According to Offeman (JAOCS, Vol. 83, No. 2 (2006), p. 153-157), the $K_{DE}=[EtOH]_{org}/[EtOH]_{aq}$, of 0.193 and a separation factor, $\alpha=K_{DE}/K_{DW}=K_{DE}/([H_2O]_{org}/[H_2O]_{aq}$, of 15.9 for with a starting ethanol concentration in the aqueous solution of 5 wt % at 33° C.

A 100 kg of 6 wt % ethanol/water solution is combined with 700 kg of neat castor oil. The feed material has 6 kg ethanol combined with 94 kg water. In a single stage cross flow extractor, the resulting castor oil/ethanol solution has 3.538 kg of ethanol, and the water-rich raffinate has 2.462 kg of ethanol. If four stages of countercurrent extraction are employed, then the castor oil/ethanol solution has 5.489 kg of ethanol and the water-rich solution has 0.511 kg of ethanol. Thus, the discharged raffinate is 0.54 wt % ethanol. This water-rich solution is returned to the fermentation broth. The castor oil/ethanol solution is subject to subsequent extraction by carbon dioxide.

The second stage of extraction uses a countercurrent column to extract the ethanol from castor oil with near-critical $CO_2$. The $CO_2$ could be at liquid or near supercritical conditions; however, preferably is liquid $CO_2$ at a pressure of 68 to 71 bar. The process conditions are established such that the density of $CO_2$ is lower than the density of the castor oil. Thus, the castor oil tends to move down the countercurrent column and be contacted with the rising near-critical $CO_2$. The ethanol is extracted from the castor oil to the liquid carbon dioxide. The castor oil, now depleted of ethanol and still nearly fully saturated with water, is returned to be combined with the stream from the fermentation bath. In this manner, the castor oil is nearly all fully recycled. At near critical conditions, $CO_2$ has limited solubility for water, so a limited quality of water is dissolved by the $CO_2$. The majority of the $CO_2$ solvent is removed to recover the ethanol. A smaller portion of the $CO_2$ stream may be returned to the column through the reflux valve. The side stream process cycle enables the $CO_2$ to be converted to a vapor at modest temperatures relative to the 78° C. boiling point for ethanol. As shown in FIG. 1, this includes a pressure reduction valve and a vaporizing heat exchanger. The $CO_2$ vapor and ethanol liquid is passed into a cyclone separator where the ethanol is removed and the $CO_2$ vapor is permitted to pass overhead. The $CO_2$ vapor is then condensed and pumped back into the process, so that the major of the $CO_2$ solvent is full recycled.

Example 2

Extraction of Ethanol from An Ethanol-Water Solution

A 10 kg of 50 wt % ethanol/water solution was combined with 20 kg of neat castor oil. The feed material had 5 kg ethanol combined with 5 kg water. A two stage counter countercurrent extraction was employed, thus creating a castor oil/ethanol solution with 3.795 kg of ethanol and the water-rich solution had 1.205 kg of ethanol. The resultant phases were separated with a centrifuge. The castor oil rich extract was 16.5% ethanol and the water-rich raffinate was 19.42% ethanol. The castor oil/ethanol solution was subject to subsequent extraction by carbon dioxide.

The second stage of extraction used a countercurrent column to extract the ethanol from castor oil with liquid $CO_2$. The liquid $CO_2$ was at 95 bar and 22° C. with a density of 0.836 kg/L. At this density, $CO_2$ is less dense than the castor oil. Castor oil was injected into a countercurrent column near the upper elevation of the countercurrent column. $CO_2$ was introduced near the bottom of the countercurrent column. The castor oil moved down the countercurrent column and was contacted with the rising near-critical $CO_2$. The column had a height equivalent to two theoretical stages. The ethanol was extracted from the castor oil to the liquid carbon dioxide. The $CO_2$ and ethanol stream was vaporized and the ethanol collected in a separator. The energy per unit quantity of the ethanol was 1821 kJ/kg. Using an Aspen distillation model, the same feed stream into a 20 theoretical stage distillation column with a reflux ratio of 2 and no preheat would be 3500 kJ/kg. Thus, the process demonstrated offered significant energy savings over known processing methods (e.g., at least about 1679 kJ/kg).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for extracting ethanol from an ethanol-water solution comprising:
   a) mixing an ethanol-water solution with a first solvent comprising an esterified fatty acid, wherein the esterified fatty acid comprises a hydroxylated fatty acid component and an alcohol component such that the alcohol component is a $C_{3-6}$ alcohol, wherein the distribution coefficient for ethanol in the mixture of the ethanol-water solution and the first solvent is at least 0.02 favoring the transfer of ethanol from the ethanol-water solution to the first solvent, thereby extracting the ethanol from the ethanol-water solution into the first solvent;
   b) separating the first solvent and the ethanol-water solution;
   c) contacting the first solvent with carbon dioxide, wherein the carbon dioxide is at a liquid or near supercritical phase, wherein the distribution coefficient for ethanol in a mixture of the first solvent and the carbon dioxide is at least 0.1 favoring the transfer of ethanol from the first solvent to the carbon dioxide, thereby extracting the ethanol from the first solvent into the carbon dioxide; and
   d) converting the carbon dioxide to vapor phase, thereby releasing the ethanol from the carbon dioxide, yielding a solution of greater ethanol concentration than the ethanol concentration in the starting ethanol-water solution.

2. The method of claim 1, wherein the ethanol-water solution comprises less than 99% ethanol (v/v).

3. The method of claim 1, wherein the ethanol-water solution is a fermentation broth.

4. The method of claim 1, wherein the hydroxylated fatty acid component of the esterified fatty acid is ricinoleic acid.

5. The method of claim 1, wherein the esterified fatty acid is a triglyceride.

6. The method of claim 5, wherein the triglyceride comprises 1 to 3 ricinoleic acid substituents.

7. The method of claim 1, wherein the alcohol component is glycerol.

8. The method of claim 1, wherein the first solvent is castor oil.

9. The method of claim 1, wherein the first solvent is contacted with the carbon dioxide in a counter current column.

10. A system for extracting ethanol from an ethanol-water solution comprising:
    a liquid feed inlet comprising the ethanol-water solution and a first solvent;
    a mixer in fluid communication with the liquid feed inlet, wherein the mixer continuously mixes the ethanol-water solution and the first solvent, wherein the ethanol-water solution comprises ethanol and the first solvent comprises an esterified fatty acid, wherein the esterified fatty acid comprises a hydroxylated fatty acid component and an alcohol component such that the alcohol component is a $C_{3-6}$ alcohol, wherein the distribution coefficient for ethanol in the mixture of the ethanol-water solution and the first solvent is at least 0.02 favoring the transfer of ethanol from the ethanol-water solution to the first solvent;
    a separation vessel in fluid communication with the mixer;
    a pressurized extraction vessel in fluid communication with with the separation vessel, wherein the extraction vessel operates at a pressure sufficient to maintain the carbon dioxide is at a liquid or near supercritical phase, wherein the transfer of ethanol from the first solvent to the carbon dioxide is effected in the extraction vessel;
    a vaporizer in fluid communication with the extraction vessel, wherein the vaporizor operates at a pressure sufficient to convert the carbon dioxide to vapor phase, wherein release of the ethanol from the carbon dioxide is effected in the vaporizer; and
    a collector in communication with the vaporizer, wherein the collector contains the ethanol released from the carbon dioxide in the vaporizer.

11. The system of claim 10, wherein the ethanol-water solution is a fermentation broth.

12. The system of claim 10, wherein the liquid feed inlet is selected from the group consisting of hose, piping and tubing.

13. The system of claim 10, wherein the mixer is an in-line mixer.

14. The system of claim 10, wherein the separation vessel is a centrifuge.

15. The system of claim 10, wherein the extraction vessel is a countercurrent column.

16. The system of claim 10, wherein the vaporizer further comprises a heat pump for the vaporization and recovery of liquid carbon dioxide.

17. The system of claim 10, wherein the collector is a cyclone separator.

18. The system of claim 10, wherein the separation vessel is in fluid communication with the liquid feed inlet for recycling the ethanol-water solution.

19. The system of claim 10, wherein the extraction vessel is in fluid communication with the liquid feed inlet for recycling the first solvent.

20. The system of claim 10, further comprising a condenser to convert the vapor phase carbon dioxide to the liquid or near supercritical phase, the condenser being configured for fluid communication with the collector.

21. The system of claim 20, wherein the condenser is in fluid communication with the extraction vessel for recycling the carbon dioxide.

22. The system of claim 10, wherein system allows for continuous flow processing.

23. The system of claim 10, wherein the ethanol is extracted without requiring distillation of ethanol from water.

* * * * *